United States Patent [19]

Ikeda et al.

[11] Patent Number: 5,420,355

[45] Date of Patent: May 30, 1995

[54] METHOD OF PRODUCING A HIGHLY PURE BORATE COMPLEX OF TRIARYLBORANE WITH ALKYLATED OR ARYLATED ALKALI METAL

[75] Inventors: Yoshihiko Ikeda, Shinnanyo; Takeo Yamane, Ogori; Eiichi Kaji; Kenji Ishimaru, both of Shinnanyo, all of Japan

[73] Assignee: Tosoh Akzo Corporation, Tokyo, Japan

[21] Appl. No.: 141,546

[22] Filed: Oct. 27, 1993

[30] Foreign Application Priority Data

Nov. 2, 1992 [JP] Japan .................................. 4-317706

[51] Int. Cl.⁶ .............................................. C07F 5/04
[52] U.S. Cl. ........................................................ 568/6
[58] Field of Search .......................................... 568/6

[56] References Cited

U.S. PATENT DOCUMENTS 3,405,179 10/1968 Wowk ...................................... 568/6

OTHER PUBLICATIONS

Negishi et al., J. C. S. Perkin II, vol. 32, p. 1225, Feb. 1978, "Scope and Reaction of Organoboranes with Organolithiums as a Method of Preparation of Lithium Organoborates. Stability of Lithium Organoborates".

Primary Examiner—Howard T. Mars
Assistant Examiner—Michael B. Hydorn
Attorney, Agent, or Firm—Oblon, Spivak, McClelland, Maier, & Neustadt

[57] ABSTRACT

A highly pure borate complex of a trialkylborane with an alkylated or arylated alkali metal is obtained by reacting an aryl magnesium halide with a boron trihalide to produce a triarylborane product. The triarylborane product is then subjected to thorough removal of magnesium salts produced as by-products and removal of unreacted aryl magnesium halide. A solution of alkylated or arylated alkali metal in a hydrocarbon solvent, a straight chain ether solvent or a mixed solvent thereof is then added dropwise to the solution of triarylborane product in a hydrocarbon solvent, straight chain ether solvent or mixed solvent thereof, while keeping the temperature range from $-80°$ to $25°$ C.

6 Claims, No Drawings

METHOD OF PRODUCING A HIGHLY PURE BORATE COMPLEX OF TRIARYLBORANE WITH ALKYLATED OR ARYLATED ALKALI METAL

BACKGROUND OF THE INVENTION

The present invention relates to a method of producing a stable highly pure product of a borate complex of triarylborane with alkylated or arylated alkali metal.

In the conventional production method of alkali metal ate complex of organoboron, generally (J. C. S. Perkin II, E. NEGISI et al., 32, 1225 (1978)), organoboron is reacted with organo alkali metal at 0° C. using tetrahydrofuran or diethyl ether as a solvent. On the other hand, when organo lithium is reacted using tetrahydrofuran as a solvent, there is a possibility of causing a side reaction as follows (J. Organo-metallic Chemistry, H. C. BROWN et al., 188, 1–10(1980)):

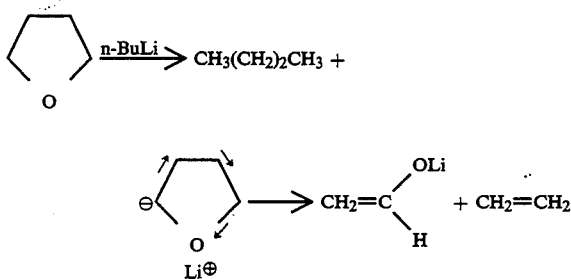

As described above, in the conventional production method of alkali metal borate complex of organoboron, generally, organoboron is reacted with organo alkali metal at 0° C. using tetrahydrofuran or diethyl ether as a solvent. Moreover, when organo lithium is reacted using tetrahydrofuran as a solvent there is a possibility to cause a side reaction.

The present invention is a result of investigations on a production method of high-yield and yet high purity borate complex of triarylborane with alkylated or arylated alkali metal. In this invention, after the synthesis of triarylborane, the ether type solvent is distilled off, thus leaving only the hydrocarbon type solvent, and then, after removing thoroughly the solidifying magnesium salt produced as a by-product and unreacted arylmagnesium halide, the triarylborane product is reacted with a solution of alkylated or arylated alkali metal in hydrocarbon type solvent, chain ether type solvent or mixed solvent thereof at −20°–5° C., thereby side reactions with the side-produced magnesium salt and the unreacted arylmagnesium halide can be prevented and, at the same time, the problems aforementioned can be solved, leading to the invention.

SUMMARY OF THE INVENTION

The invention provides a production method characterized in that after removing thoroughly a side-produced magnesium salt and unreacted arylmagnesium halide from triarylborane product obtained by reaction of arylmagnesium halide with boron trihalide, a solution of alkylated or arylated alkali metal in hydrocarbon type solvent, chain ether type solvent or mixed solvent thereof is added dropwise to a solution of the triarylborane product in hydrocarbon type solvent, chain ether solvent or mixed solvent thereof to react while keeping a temperature range from −80° to 25° C., thereby producing a highly pure borate complex of trialkylborane with alkylated or arylated alkali metal.

DETAILED DESCRIPTION OF THE INVENTION

In following, the invention will be illustrated in detail.

The triarylboranes are boron compounds represented by a general formula (I)

$$R^1{}_3B \qquad (I)$$

Many anionic species such as a carbanion and an alkoxy anion can attach to 3-coordination metals such as boron and aluminum to form stable 4-coordination metal anions (II) called ate complex.

$$R^1{}_3B + R^2M \rightarrow [R^1{}_3B^- \text{-} R^2]M^+ \qquad (II)$$

In the general formula above, $R^1$=aryl group, $R^2$=alkyl group or aryl group and M=alkali metal.

Suitable aryl group include phenyl group, tolyl group, xylyl group, mesityl group, biphenyl group, naphthyl group, anthryl group, phenanthryl group, pentafluorophenyl group, tris-(trifluoromethyl) phenyl group, etc. fall thereunder. Further, exemplifying some of alkyl groups, methyl group, ethyl group, propyl group, isopropyl group, butyl group, sec-butyl group, isobutyl group, tert-butyl group, pentyl group, isopentyl group, neopentyl group, hexyl group, cyclohexyl group, heptyl group, octyl group, isooctyl group, etc. fall thereunder. Suitable alkali metals include, lithium, sodium, potassium, etc. fall thereunder and lithium is preferable, because of stability of alkylated or arylated alkali metal which is the precursor.

In the invention, an excess of arylmagnesium halide above the theoretical amount is required to obtain (I) stably in high yield and high purity when equation (II) proceeds.

The effect of temperature on the side reactions of the unreacted aryl magnesium halide was ascertained (following general equations (III) and (IV)). Further, concerning halogenated magnesium salt, the same side-reaction as that of arylmagnesium halide also takes place. By reacting within a temperature range from −80° to 25° C., it is possible to synthesize a highly pure borate complex of triaryl-borane with alkylated or arylated alkali metal.

$$R^1MgBr + R^2 - M \rightarrow R^1 - M + R^2MgBr \qquad (III)$$

$$R^1{}_3B + R^1 - M \rightarrow [R^1{}_4B^-]M^+ \qquad (IV)$$

Therefore, triarylborane employed as the raw material of this reaction requires one in which halogenated magnesium salt side-produced at the time of producing triarylborane itself and unreacted arylmagnesium halide are thoroughly removed.

In the invention, the temperature of reaction between the toluene solution of triarylborane containing unreacted aryl-magnesium halide and alkylated or arylated alkali metal was investigated when equation (II) proceeds.

With respect to the reaction solvent, where an ether type solvent is employed, it should be a chain ether type solvent, to avoid formation of borate complexes having a composition ratio outside of the substituent ratio 3:1, which is the ratio of the four substituents bonded to boron, that is, the ratio of the number of original aryl groups of the triarylborane to the alkyl group or aryl group introduced later by the alkylated or arylated alkali metal, when tetrahydrofuran exists in the reaction system. However, alkylated or arylated alkali metal can be prepared without employing the ether-type solvent, so an ether-type solvent is not mandatory to the reaction.

In the following, the invention will be illustrated in more detail based on the examples, but the invention is not subject to the restriction by following examples at any rate, so long as the gist is not exceeded.

The determination of purity in following examples was made by areal percentage method using liquid chromatography. Moreover, the abbreviations here are shown below.

$Ar4 = [R^1_4B^-]M^+$ $Ar3 = [R^1_3B^-R^2]M^+$ $Ar2 = [R^1_2B^-R^2_2]M^+$ $Ar1 = [R^1B^-R^2_3]M^+$

EXAMPLE 1

A 50 mL three-neck round bottom flask was equipped with a 50 mL glass dropping funnel, and flushed with nitrogen. Thereafter, 30 mL of toluene and 2.78 g (0.0196 mol) of boron trifluoride ethyl ether complex were charged into the flask. Into the dropping funnel were charged 38.49 g (0.0743 mol) of 35 wt. % ethyl ether solution of phenyl-magnesium bromide. The ethyl ether solution of phenyl-magnesium bromide was added dropwise from dropping funnel to the reactor under stirring. The reaction temperature at that time was 20° to 30° C.

After the completion of dropwise addition, the reactor was heated to 110° C. to remove ethyl ether. Aging was performed for 2 hours at that temperature, producing magnesium bromide fluoride as a by-product. The filterable suspended magnesium bromide fluoride was removed with a glass filter. The toluene solution of triphenylborane thus obtained was charged into a 200 mL three-neck round bottom flask flushed with nitrogen. Into the reactor with stirring, a 24 wt. % hexane solution of butyl lithium was charged with a syringe in an amount of 1.1 times the mole equivalent weight based on boron trifluoride ethyl ether complex used on synthesizing triphenylborane. The reaction temperature at that time was −40° C. (±2° C.).

After the completion of dropwise addition, aging was performed for 30 minutes at the same temperature and then hydrolysis was conducted below 10° C. The organic layer was extracted twice with distilled water. From the combined aqueous layers, the purity of butyl triphenylborate which is a borate complex of triphenylborane was determined by means of liquid chromatography prepared. The results are shown in Table 1.

EXAMPLE 2

A 50 mL three-neck round bottom flask was equipped with a 50 mL glass dropping funnel, and was flushed with nitrogen. Thereafter, 30 mL of toluene and 2.78 g (0.0196 mol) of boron trifluoride ethyl ether complex were charged into the flask. Into the dropping funnel were charged 38.49 g (0.0743 mol) of 35 wt. % ethyl ether solution of phenyl-magnesium bromide. The ethyl ether solution of phenyl-magnesium bromide was added dropwise from the dropping funnel to the reactor under stirring. The reaction temperature at that time was 20° to 30° C.

After the completion of dropwise addition, the reactor was heated to 110° C. to remove ethyl ether. Aging was performed for 2 hours at that temperature, producing magnesium bromide fluoride as a by-product. The filterable suspended, magnesium bromide fluoride was removed with a glass filter. The toluene solution of triphenylborane thus obtained was charged into a 200 mL three-neck round bottom flask flushed with nitrogen. Into the reactor under stirring, was charged a 24 wt. % hexane solution of butyllithium with a syringe in an amount of 1.1 times the mole equivalent weight based on boron trifluoride ethyl ether complex used on synthesizing triphenylborane. The reaction temperature at that time was 0° C. (±5° C.).

After the completion of dropwise addition, aging was performed for 30 minutes at the same temperature and then hydrolysis was conducted below 11° C. The organic layer was extracted twice with distilled water. From the combined aqueous layers, the purity of butyl triphenylborate which is a borate complex of triphenylborane was determined by means of liquid chromatography prepared. The results are shown in Table 1.

COMPARATIVE EXAMPLE 1

A 50 mL three-neck round bottom flask was equipped with a 50 mL glass dropping funnel, and was flushed with nitrogen. Thereafter, 30 mL of toluene and 2.78 g (0.0196 mol) of boron trifluoride ether complex were charged into the flask. Into the dropping funnel were charged 38.49 g (0.0743 mol) of 35 wt. % ethyl ether solution of phenylmagnesium bromide. The ethyl ether solution of phenylmagnesium bromide was added dropwise from the dropping funnel to the reactor under stirring. The reaction temperature at that time was 20° to 30° C.

After the completion of dropwise addition, the reactor was heated to 110° C. to remove ethyl ether. Aging was performed for 2 hours at that temperature, producing magnesium bromide fluoride as a by-product. The filterable suspended, magnesium bromide fluoride was removed with a glass filter. The toluene solution of triphenylborane thus obtained was charged into a 200 mL three-neck round bottom flask replaced flushed with nitrogen. Into the reactor under stirring, was charged a 24 wt. % hexane solution of butyllithium with a syringe in an amount of 1.1 times the mole equivalent weight based on boron trifluoride ethyl ether complex used on synthesizing triphenylborane. The reaction temperature at that time was 25° to 35° C.

After the completion of dropwise addition, aging was performed for 30 minutes at the same temperature and then hydrolysis was conducted below 8° C. The organic layer was extracted twice with distilled water. From the combined aqueous layers, the purity of butyl triphenylborate which is a horate complex of triphenylborane was determined by means of liquid chromatography prepared. The results are shown in Table 1.

COMPARATIVE EXAMPLE 2

A 50 mL three-neck round bottom flask was equipped with a 50 mL glass dropping funnel, and was flushed with nitrogen. Thereafter, 30 mL of tetrahydrofuran and 2.78 g (0.0196 mol) of boron trifluoride ethyl ether complex were charged into the flask. Into the dropping funnel were charged 38.49 g (0.0743 mol) of 35 wt. % ethyl ether solution of phenylmagnesium bromide. The ethyl ether solution of phenylmagnesium bromide was added dropwise from the dropping funnel to the reactor under stirring. The reaction temperature at that time was 20° to 30° C.

After the completion of dropwise addition, the reactor was heated to 66° to 69° C. to remove ethyl ether. Aging was performed for 2 hours at that temperature, producing magnesium bromide fluoride as a by-product. The filtrable suspended magnesium bromide fluoride was removed with a glass filter. The tetrahydrofuran solution of triphenylborane thus obtained was charged into 200 mL three-neck round bottom flask flushed with nitrogen. Into the reactor under stirring, was charged a 24 wt. % hexane solution of butyl lithium with a syringe in an amount of 1.1 times the mole equivalent weight based on boron trifluoride ethyl ether complex used on synthesizing triphenylborane. The reaction temperature at that time was 25° to 35° C.

After the completion of dropwise addition, aging was performed for 30 minutes at the same temperature and then hydrolysis was conducted below 8° C. The organic layer was extracted twice with distilled water. From the combined aqueous layers, the purity of butyl triphenylborate which is are complex of triphenylborane was determined by means of liquid chromatography prepared. The results are shown in Table 1.

added with a solution of N,N-dimethylanilinium chloride to give a compound of N,N-dimethylanilinium tetrakis (pentafluorophenyl) borate, of which dry weight was 85% of theoretical value, and yield was 85% from determination by fluorine nuclear magnetic resonance spectrum employing pentafluorotoluene as an internal standard substance.

EXAMPLE 4

A 200 ml glass flask was equipped with a 50 ml glass dropping funnel, and was flushed with nitrogen. Then, 30 ml of toluene degassed fully with nitrogen and 2.78 g (0.0196 mol) of boron trifluoride ethyl ether complex were charged into the flask. Further, into the dropping funnel were charged 61.42 g (0.0619 mol) of 20 wt. % ethyl ether solution of p-tolylmagnesium bromide. The ethyl ether solution of the p-tolylmagnesium bromide was added dropwise from the dropping funnel into the flask under stirring. The reaction temperature at that time was about 20°–30° C., which was hardly exothermic. After the completion of dropwise addition, the flask was heated to remove ethyl ether.

After the temperature of the flask was elevated up to the boiling point, aging was performed for three hours at that temperature and, after magnesium bromide fluoride was solidified, the magnesium bromide fluoride was removed with glass filter. To the light yellow transparent reaction liquid was added butyl lithium at −20°

|  | Synthesizing conditions | | | | Composition ratio (Area %) | | | |
| --- | --- | --- | --- | --- | --- | --- | --- | --- |
| Example | Reaction temperature (°C.) | Stirring temperature (°C.) | Time (hr) | Hydrolysis (°C.) | Ar4 (%) | Ar3 (%) | Ar2 (%) | Ar1 (%) |
| Example 1 | −40 ± 2 | −40 ± 2 | 0.5 | 0–10 | 0 | 96.6 | 0.9 | 1.2 |
| Example 2 | 0 ± 5 | 0 ± 5 | 0.5 | 0–11 | 0 | 98.0 | 0.4 | 0.7 |
| Comparative example 1 | 25–35 | 25–35 | 0.5 | 0–8 | 6.0 | 89.2 | 1.0 | 1.0 |
| Comparative example 2 | 25–35 | 25–35 | 0.5 | 0–8 | 14.0 | 80.2 | 1.2 | 1.0 |

Evidently from Table 1, according to the invention, it can be seen that a highly pure borate complex of triphenylborane is obtained.

EXAMPLE 3

A 200 ml glass flask was equipped with a 50 ml glass dropping funnel, and was flushed with nitrogen. Then, 30 ml of toluene degassed fully with nitrogen and 2.78 g (0.0196 mol) of boron trifluoride ethyl ether complex were charged into the flask. Further, into the dropping funnel were charged 84.99 g (0.0627 mol) of 20 wt. % ethyl ether solution of pentafluorophenylmagnesium bromide. The ethyl ether solution of pentafluorophenylmagnesium bromide was added dropwise from the dropping funnel into the flask under stirring. The reaction temperature at that time was about 26° C., which was hardly exothermic. After the completion of dropwise addition, the flask was heated to remove ethyl ether.

After the temperature of the flask was elevated up to the boiling point of toluene, aging was performed for one to three hours at that temperature and, after magnesium bromide fluoride was solidified, the magnesium bromide fluoride was removed with glass filter. With the light brown reaction liquid was reacted pentafluorophenyl lithium which was prepared at −70° C. in a mixed solvent of ethyl ether-hexane from pentafluorophenyl bromide and butyl lithium, and then C. to give a stable complex, from which the yield was determined to be 89.6% and the purity was measured to be 91.6% in areal percentage using liquid chromatography.

As described, according to the invention, it becomes possible to produce high-purity stable borate complex of triarylborane with alkylated or arylated alkali metal stably.

What is claimed is:

1. A method for producing a borate complex of a triaryl borane with an alkyl or aryl alkali metal, comprising the steps of:

(a) reacting an arylmagnesium halide with a boron trihalide in a molar ratio of 3.158–3.790:1 in a reaction solvent consisting essentially of a hydrocarbon solvent, a straight chain ether solvent or mixture thereof to form a triaryl borane solution containing unreacted arylmagnesium halide and magnesium halide salts;

(b) removing by distillation said straight chain ether solvent from said triarylborane solution when said straight chain ether solvent is present in said reaction solvent;

(c) solidifying the unreacted arylmagnesium halide and magnesium salts in said triarylborane solution and removing these solids from the triarylborane solution to form a purified triarylborane solution; and (d) contacting said purified triarylborane solution with an alkyl or aryl alkali metal to form a solution of said borate complex.

2. The method of claim 1, wherein one equivalent of said purified triarylborane is contacted with 1.1 equivalent of said alkyl or aryl alkali metal in said contacting step (d).

3. The method of claim 1, wherein said contacting step is conducted at a temperature of −80° C. to 5° C.

4. The method of claim 3, wherein said contacting step is conducted at a temperature from −20° C. to 5° C.

5. The method of claim 3, further comprising (e) stirring said borate complex solution at a temperature of −80° C. to 5° C. and then subjecting the stirred solution to hydrolysis at a temperature of −80° C. to 5° C.

6. The method of claim 1, wherein said reaction solvent is a hydrocarbon solvent.

* * * * *